United States Patent [19]

Griffith et al.

[11] 4,102,873
[45] Jul. 25, 1978

[54] ELECTRICAL CONDUCTING PHTHALONITRILE POLYMERS

[75] Inventors: James R. Griffith, Riverdale Heights; Jacques G. O'Rear, Temple Hills, both of Md.

[73] Assignee: The United States of America as represented by the Secretary of the Navy, Washington, D.C.

[21] Appl. No.: 843,907

[22] Filed: Oct. 20, 1977

Related U.S. Application Data

[62] Division of Ser. No. 681,087, Apr. 28, 1976, Pat. No. 4,057,569.

[51] Int. Cl.² ............................................. C08G 73/00
[52] U.S. Cl. ...................................... 528/331; 528/362
[58] Field of Search .................. 260/78.41, 67 R, 72.5

[56] References Cited

U.S. PATENT DOCUMENTS

| | | | |
|---|---|---|---|
| 3,182,039 | 5/1965 | Remy | 260/67 R X |
| 3,281,394 | 10/1966 | Katon | 260/67 R |
| 3,282,931 | 11/1966 | Zienty et al. | 260/47 EP X |
| 3,336,261 | 8/1967 | Smith et al. | 260/67 R X |
| 3,418,281 | 12/1968 | Smith et al. | 260/72.5 |
| 3,493,524 | 2/1970 | Webb | 260/67 R X |
| 3,503,739 | 3/1970 | DuBosc et al. | 260/72.5 X |
| 3,993,631 | 11/1976 | Griffith et al. | 260/78 TF |

*Primary Examiner*—Lucille M. Phynes
*Attorney, Agent, or Firm*—R. S. Sciascia; Philip Schneider; Thomas McDonnell

[57] ABSTRACT

Compounds of the general formula:

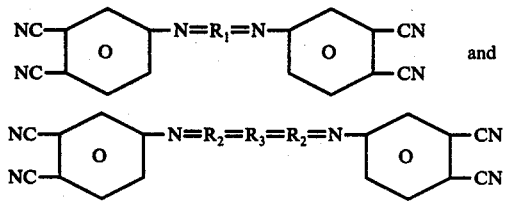

wherein $R_1$ is an isomer of phthalaldehyde; $R_2$ is an isomer of an aromatic dialdehyde selected from the class consisting of phthalaldehyde, naphthalene dialdehyde, phenanthrene dialdehyde, anthracene dialdehyde, biphenyl dialdehyde, terphenyl dialdehyde; and mixtures thereof and $R_3$ is an isomer of an aromatic diamine selected from the class consisting of benzene diamine, naphthalene diamine, phenanthrene diamine, biphenyl diamine, and terphenyl diamine, and the cyano-condensation resins thereof which are useful in preparing semiconductors.

9 Claims, No Drawings

ELECTRICAL CONDUCTING PHTHALONITRILE POLYMERS

This is a division of application Ser. No. 681,087 filed on Apr. 28, 1976, now U.S. Pat. No. 4,057,569.

BACKGROUND OF THE INVENTION

This invention pertains generally to organic polymers and in particular to organic semiconductors.

A semiconductor is a near insulator at room temperature. At this temperature the resistivity of a semiconductor is from $10^{-2}$ to $10^{+9}$ ohm cm.

Until recently organic polymers were generally considered to be very poor conductors of electricity. Newly discovered organic polymers, however, have shown promise as semiconductors. These polymers have the disadvantages of low molecular weight and poor moldability.

SUMMARY OF THE INVENTION

It is therefore an object of this invention to provide a class of high molecular weight polymeric semiconductors which can be processed into convenient shapes by conventional resin technology.

Another object of this invention is to provide polymeric semiconductors with low resistivity and high structural strength.

These and other objects are achieved by a heat-treated totally conjugated cyano-condensation resin of bisorthodinitrile selected from the class consisting of

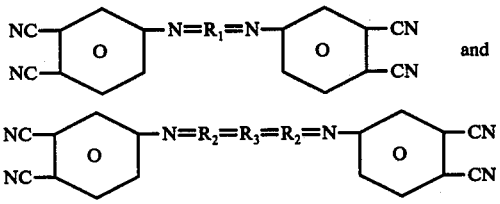

and

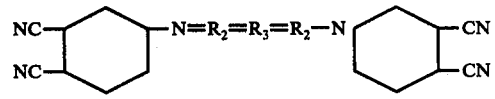

wherein $R_1$ is an isomer of phthalaldehyde; $R_2$ is an isomer of an aromatic dialdehyde selected from the class consisting of phthalaldehyde, naphthalene dialdehyde, phenanthrene dialdehyde, anthracene dialdehyde, biphenyl dialdehyde, and terphenyl dialdehyde; and $R_3$ is an isomer of an aromatic diamine selected from the class consisting of benzene diamine, naphthalene diamine, phenanthrene diamine, biphenyl diamine, and terphenyl diamine. Such high molecular weight totally conjugated resins provide excellent conductivity through the large number of $\pi$-electrons and by the absence of a separation between the conjugate bonds.

DETAILED DESCRIPTION OF THE INVENTION

The bisorthodinitriles of the general formula:

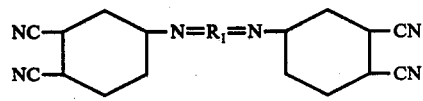

are prepared by reacting 4-aminophthalonitrile with the appropriate isomer of phthalaldehyde in a refluxing solvent. The synthesis involving p-phthalaldehyde proceeds accordingly:

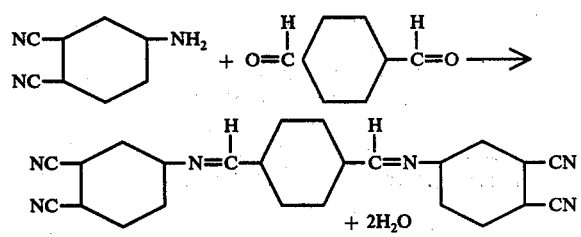

The bisorthodinitriles of the general formula:

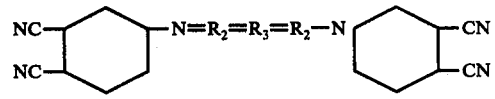

are prepared by reacting 4-aminophthalaldehyde with an aldehydeterminated Shiff base (anil) of the general formula: $R_2=R_3=R_2$ in a refluxing solvent. An example of this synthesis is as follows:

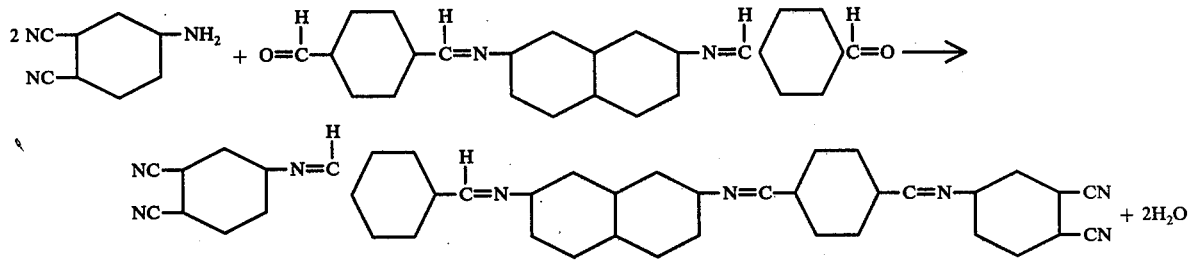

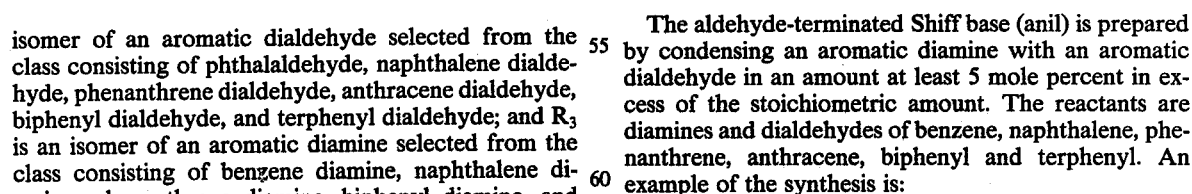

The aldehyde-terminated Shiff base (anil) is prepared by condensing an aromatic diamine with an aromatic dialdehyde in an amount at least 5 mole percent in excess of the stoichiometric amount. The reactants are diamines and dialdehydes of benzene, naphthalene, phenanthrene, anthracene, biphenyl and terphenyl. An example of the synthesis is:

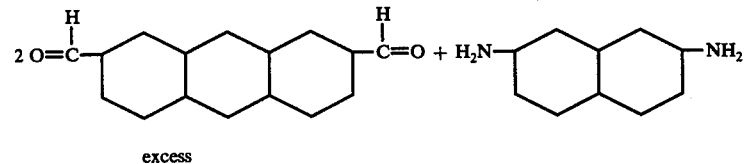

excess

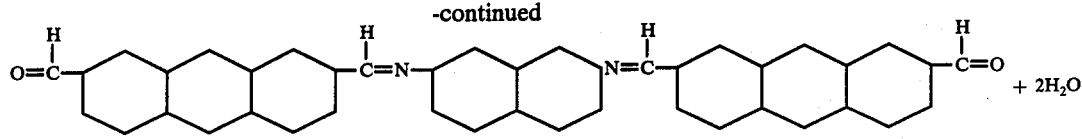

In order to decrease the reaction time for the synthesis of either of the general compounds of this invention, a stoichiometric excess of 4-aminophthalonitrile is used. The preferred excess is from 5 to 15 mole percent of the stoichiometric amount, which is two moles of 4-aminophthalonitrile for each mole of the aldehyde terminated reactant. The reactant time can be further reduced by the inclusion of a catalyst such as p-toluenesulfonic acid monohydrate. The refluxing can be carried out with any of the usual refluxing fluids. The most common fluids are preferred, such as, toluene, chlorobenzene, and methyl phenyl ether (anisole). The end point of the reaction can be easily determined by monitoring the by-product, water, or one of the reactants.

The general nature of the preparation of the bisorthodinitrile have been set forth, the following examples are presented as specific illustrations thereof. It is understood that the invention is not limited to these examples but is susceptible to different modifications that would recognized by one of ordinary skill in the art.

EXAMPLE I

Preparation of Bis(3,4-dicyanoaniline) N,N'-p-xylylenediidene

A 2-liter flask was equipped with Dean and Stark distilling trap and a water-cooled condenser and then charged with p-phthalaldehyde (8.05 g; 0106 mole), 4-aminophthalonitrile (18.90 g; 0.132 mole) and toluene (946 ml). The stirred reaction mixture was refluxed 10 hours. At this point, water (2.0 ml) had collected in the distilling trap (theory, 2.16 ml). The heavy yellow precipitate from the cooled reaction mixture was collected by filtration, washed with toluene (200 ml), and dried. This yellow residue was extracted with boiling acetonitrile (2 × 600 ml) leaving, after drying, 11.1 g of the analytical anil, mp 272°–275° C. Cooling the resulting filtrate to 0° C deposited additional crystals, which were collected and dried to give 8.9 g more of the analytical anil, mp 272°–275° C; total yield 20.0 g (86.7%); Anal. calcd. for $C_{24}H_{12}N_6$: C, 74.99; H, 30.4; N, 21.86; Found: C, 74.94; H, 3.04; N, 21.94. Note: The above anil can be recrystallized from anisole.

EXAMPLE II

Catalyzed preparation of Bis(3,4-dicyanoaniline) N,N'-p-xylyenediidene

A 2-liter flask was equipped with Dean and Stark distilling trap and a water-cooled condenser and then charged with p-phthalaldehyde, (8.05 g; 0.06 mole), 4-aminophthalonitrile (18.90 g; 0.06 mole), 4-aminophthalonitrile (18.90 g; 0.132 mole) p-toluene-sulfonic acid monohydrate (0.03 g.). The results were identical to Example I.

EXAMPLE III

Preparation of Bis(3,4-dicyanoaniline) N,N'm-xylylenediidene

The corresponding m-isomer, i.e., bis(3,4-dicyanoaniline) N,N'-m-xylylenediidene was prepared in a similar way. The reaction change was m-phthalaldehyde (4.80 g; 0.358 mole), 4-aminophthalinitrile (11.27 g; 0787 mole), 0.02 g p-toluenesulfonic acid monohydrate and toluene (474 ml). Refluxing the reaction mixture for 4 hours removed 1.1 ml of water (theory 1.3 ml). Filtration of the reaction mixture 60° C) left a pale yellow residue after drying of 13.6 g, m.p. 253°–257° C, 98.9% yield, pure enough for most purposes. Recrystallion from anisole or from a 50:50 volume mixture of toluene: pyridine leads to the analytical m-dianil, m.p. 254°–258°:

EXAMPLE IV

Preparation of

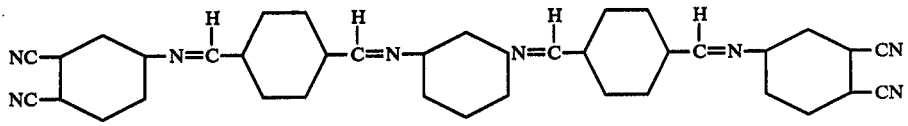

A. Preparation of the aldehyde-terminated Shiff base (anil)

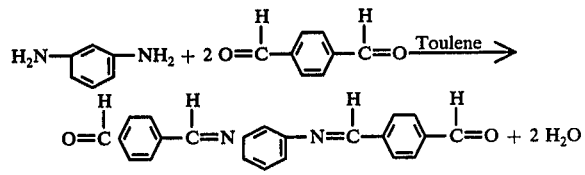

A charge of m-phenylenediamine (4.03 g; .0373 mole), p-phthalaldehyde (12.70 g; .0946 mole) and 1000 ml of toluene was stirred and refluxed using a Dean and Stark water distillation trap. After 3 hours 1.00 ml of water was collected (1.34 ml theory). This gave the crude polymeric aldehyde terminated anil.

B. Preparation of the Bisorthodimitrile

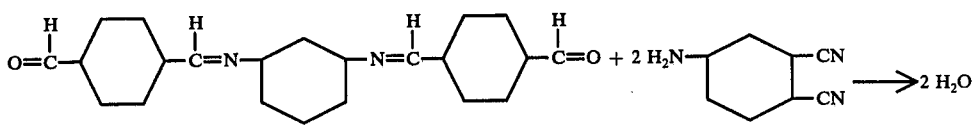

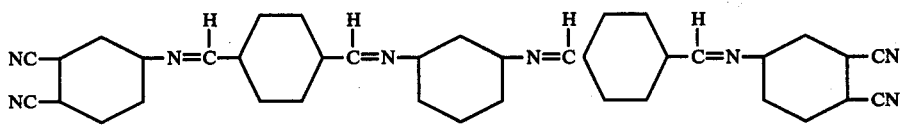

To the reaction solution of part A 4-aminophthalanitrile (11.75 g; 0.0820 mole) was added, and stirring and refluxing was continued for 16 hours. An additional 1.20 ml of water accumulated in the water trap. The hot reaction mixture (80° C) was filtered to get 13.4 g of yellow crystals (mp 225°-245° C). To assure complete reaction this residual was combined with 4.00 g of 4-aminophthalonitrile and toluene (473 ml). Further refluxing and stirring led to the removal of 0.1 ml water. Filtering at 80° C left 10.0 of yellow crystals. Extraction with boiling acetonitrile (200 ml) left 8.07 g of yellow crystals containing no $NH_2$ or CHO groups by(Infrared Spectroscopy), , m.p. 235°-250° C.

A cyano-condensation resin of this invention is synthesized by simply heating one of the aforedescribed bisorthodinitrile above the melting point in an inert atmosphere, such as a vacuum from 1 to 10 mm Hg, or aragon, or nitrogen. The preferred temperature is from 1° to 30° C above the melting point of the compound and the most preferred is from 5° to 15° C higher. Gelation generally occurs after 3 to 5 hours. The heating is continued for at least another 20-25 hours in order to cure the product to a hard resin. The optimum cure time would have to be determined empirically for each resin. Prior to synthesis, it is preferred that the bisorthodinitrile is outgassed by heating the material to a melt under a vacuum. The preferred vacuum is from 1 to 10 mm Hg and the preferred time is from 15 to 20 minutes.

A cyano-condensation resin is also produced with the inclusion of certain metals and salts with the bisorthodinitrile. The inclusion of a metal or a metal salt causes the reaction to proceed quicker. Generally the resins gel and cure from about 10 to 25 percent faster. The optimum cure for any particular resin is, of course, determined by the testing of structural strength of the resins samples over a range of cure times. The preferred amount of metal or metal salt is the stoichiometric amount, i.e., one at. wt. of metal or one mole of salt for each two moles of bisorthodinitrile. If an excess of a metal or a salt, especially a salt is used, foaming results. Exemplary of metals which may be used are chromium, molybdenum, vanadium, beryllium, silver, mercury, aluminum, tin, lead, antimony, calcium, barium, manganese, magnesium, zinc, copper, iron, cobalt, nickel, palladium, and platinum. Mixtures of these metals may also be used. The preferred metals are copper, silver, and iron.

Suitable metal salts include cuprous chloride, cuprous bromide, cuprous cyanide, cuprous ferricyanide, zinc chloride, zinc bromide, zinc iodide, zinc cyanide, ferrocyanide, zinc acetate, zinc sulfide, silver chloride, ferrous chloride, ferric chloride, ferrous ferricyanide, ferrous chloroplatinate, ferrous fluoride, ferrous sulfate, cobaltous chloride, cobaltic sulfate, cobaltous cyanide, nickel chloride, nickel cyanide, nickel sulfate, nickel carbonate, stannic chloride, stannous chloride hydrate, a complex of triphenylphosphine oxide and stannous chloride ($2TPPO/SnCl_2$) and mixtures thereof. The preferred salts are cuprous chloride, stannic chloride, stannous chloride hydrate, and ferrous fluoride. The cyano-condensation resins formed with metal salts have the disadvantage of air spaces in the resin caused by foaming during the preparation. As a consequence resins with a metal salts are not as important as the plain resins or the resins with a metal.

In summary the preparation of cyano-condensation resins with a metal or a salt comprises mixing a bisorthodinitrile with a salt or metal, outgassing the mixture as previously described, and heating the mixture to a temperature above the melting point of the bisorthodinitrile. The preferred and most preferred temperatures are the same as those for the syntheses without metal or salts. Since the salt or metal becomes part of the cyano-condensation resin, decreasing the particle size provides a more efficient utilization of the salt or metal. Thus particle sizes up to 2000 μ are preferred. The preferred amount of the salt or metal is the stoichiometric amount.

The following examples are given to illustrate the preparation of the cyano-condensation resins of this invention and are not intended to the limit the specification or the claims to follow:

EXAMPLE V

Preparation of the Cyano-Condensation Resin from Bis(3,4-dicyanoaniline) N,N'-p-xylylenediidene A 1-gram sample of the above bisorthodinitrile, prepared according to the method of Example II, was heated at 270° C for 24 hours. A hard dark brown resinous material resulted.

EXAMPLE VI

Preparation of the Cyano-Condensation Resin from Bis(3,4-dicyanoaniline) N,N'-p-xylylenediidene and copper A 1-gram sample of the above bisorthodinitrile, prepared according to the method of Example II was mixed with activated copper powder in a dinitrile-to-copper mole ratio of 1:2. The mixture was heated at 270° C for 18 hours. A hard dark brown resinous material was formed.

EXAMPLE VII

Preparation of the Cyano-Condensation Resin from

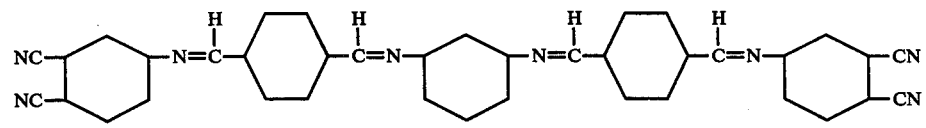

A 1-gram sample of the bisorthodinitrile, prepared in Example IV was heated at 270° C for 24 hours. A hard dark brown resinous material was formed.

The examples show that a brown colored resin is formed. It is on account of the brown color rather than a green color that it is believed that a phthalocyanine resin is not formed. The exact chemical identity of the resin is not known other than the resin is a cyano-condensation compound.

After cure, the resin is heated further at a temperature from 350° to 500° C for at least 12 hours and preferably for 18 hours, in an inert atmosphere, e.g., argon, a vacuum, or nitrogen. This last heat treatment greatly improves the electrical conductivity of the resin, but does cause a slight weight loss.

Samples of the bisorthodintrile of Example I were mixed with copper flake and cured according to the method of Example VI. The samples were then given a final cure for 18 hours at the specified temperature. The conductivities of these resins are listed in Table I. As is shown in Table I, the best results are achieved with a stoichiometric amount of copper and high final cure temperature.

Table I

| Sample No. | Cu/BODN Mole Ratio | Final Cure Temp., °C | Condutivity ohm-con |
|---|---|---|---|
| 1 | 1/1 | 300 | $7.10^8$ |
| 2 | 1/1 | 450 | $7.9 \times 10^8$ |
| 3 | 1/2 | 450 | $5.4 \times 10^7$ |

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A cyano-condensation resin obtained by heating one or more bisorthodinitriles of the general formula

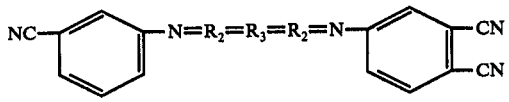

wherein $R_2$ is an isomer of an aromatic dialdehyde selected from the class consisting of phthalaldehyde, napthalene dialdehyde, phenanthrene dialdehyde, anthracene dialdehyde, diphenyl dialdehyde and terphenyl dialdehyde; and $R_3$ is an isomer of an aromatic diamine selected from the class consisting of benzene diamine, napthalene diamine, phenanthrene diamine, biphenyl diamine, terphenyl diamine to a temperature above the melting point thereof.

2. The cyano-condensation resin obtained by heating one or more bisorthodinitriles of claim 1 above the melting point thereof.

3. The cyano-condensation resin obtained by heating one or more bisorthodinitrile of claim 1 above the melting point thereof.

4. The cyano-condensation resin obtained by mixing one or more bisorthodinitriles of claim 1 with a metal selected from the class consisting of chromium, molybdenum, vanadium beryllium, silver, mercury, aluminum, tin, lead, antimony, calcium, barium, manganese, magnesium, zinc, copper, iron, cobalt, nickel, palladium, and platinum and heating said mixture above the melting point of said bisorthodinitriles.

5. The cyano-condensation resin of claim 4 wherein said metal is selected from said class consisting of copper, silver, and aluminum.

6. The cyano-condensation resin obtained by mixing one or more bisorthodinitrile of claim 1 with a salt from the class consisting of cuprous chloride, cuprous bromide, cuprous cyanide, cuprous ferricyanide, zinc chloride, zinc bromide, zinc iodide, zinc cyanide, ferricyanide, zinc acetate, zinc sulfide, silver chloride, ferrous chloride, ferric chloride, ferrous ferricyanide, ferrous chloroplatinate, ferrous fluoride, ferrous sulfate, cobaltous chloride, cobaltic sulfate, cobaltous cyanide, nickel chloride, nickel cyanide, nickel sulfate, nickel carbonate, stannic chloride, stannous chloride hydrate, a complex of triphenylophosphine oxide and stannous chloride ($2TPPO/SnCl_2$) and heating said mixture above the melting point of said bisorthodinitrile.

7. The semiconductor resin obtained by heating the cyano-condensation resin of claim 1 to a temperature from 350° C to 500° C for at least 12 hours in an inert atmosphere.

8. The semiconducting resin obtained by heating the cyano-condensation resin of claim 4 at a temperature from 350° C 500° C for at least 12 hours in an inert atmosphere.

9. The semiconducting resin obtained by heating the cyano-condensation resin of claim 6 at a temperature from 350° C to 500° C for at least 12 hours in an inert atmosphere.